(12) United States Patent
Kang et al.

(10) Patent No.: US 8,691,978 B2
(45) Date of Patent: Apr. 8, 2014

(54) COPPER PHTHALOCYANINE COMPOUNDS AND NEAR-INFRARED ABSORPTION FILTER USING THE SAME

(75) Inventors: Ju-Sik Kang, Gyeonggi-do (KR);
Jeong-Ho Park, Gyeonggi-do (KR);
Yu-Mi Chang, Gyeonggi-do (KR)

(73) Assignee: SK Chemicals Co., Ltd., Suwon-Si (KR)

( * ) Notice: Subject to any disclaimer, the term of this patent is extended or adjusted under 35 U.S.C. 154(b) by 215 days.

(21) Appl. No.: 13/142,719

(22) PCT Filed: Nov. 5, 2009

(86) PCT No.: PCT/KR2009/006495
§ 371 (c)(1),
(2), (4) Date: Jun. 29, 2011

(87) PCT Pub. No.: WO2010/076969
PCT Pub. Date: Jul. 8, 2010

(65) Prior Publication Data
US 2011/0269952 A1    Nov. 3, 2011

(30) Foreign Application Priority Data
Dec. 31, 2008   (KR) .................. 10-2008-0138395

(51) Int. Cl.
*C09B 47/04*    (2006.01)

(52) U.S. Cl.
USPC ........................................ 540/140

(58) Field of Classification Search
USPC ........................................ 540/140
See application file for complete search history.

(56) References Cited

U.S. PATENT DOCUMENTS

| 5,359,056 | A | 10/1994 | Kaieda et al. |
| 6,468,713 | B1 | 10/2002 | Terao et al. |
| 7,238,801 | B2 | 7/2007 | Masuda et al. |

FOREIGN PATENT DOCUMENTS

| JP | 09-279125 | | 10/1997 |
| JP | 11-293135 | | 10/1999 |
| JP | 2000-281919 | A | 10/2000 |
| JP | 2006-139213 | | 6/2006 |
| JP | 2007-56105 | A | 3/2007 |
| JP | 2007-169658 | A | 7/2007 |
| JP | 2008-201952 | A | 9/2008 |
| KR | 10-744718 | B1 | 8/2007 |

*Primary Examiner* — Brian McDowell
(74) *Attorney, Agent, or Firm* — Birch, Stewart, Kolasch & Birch, LLP

(57) ABSTRACT

A novel copper phthalocyanine compound with low absorptivity in the visible light region and high absorptivity in the near-infrared light region, and a near-infrared absorption filter using the same are disclosed. The near-infrared absorption copper phthalocyanine compound is represented by the following Formula 1,

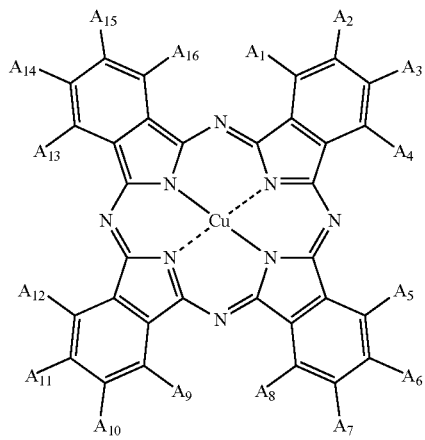

wherein, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least two thereof are $NR_3R_4$, and at least four thereof are $OR_1$; $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms.

6 Claims, 1 Drawing Sheet

Fig. 1
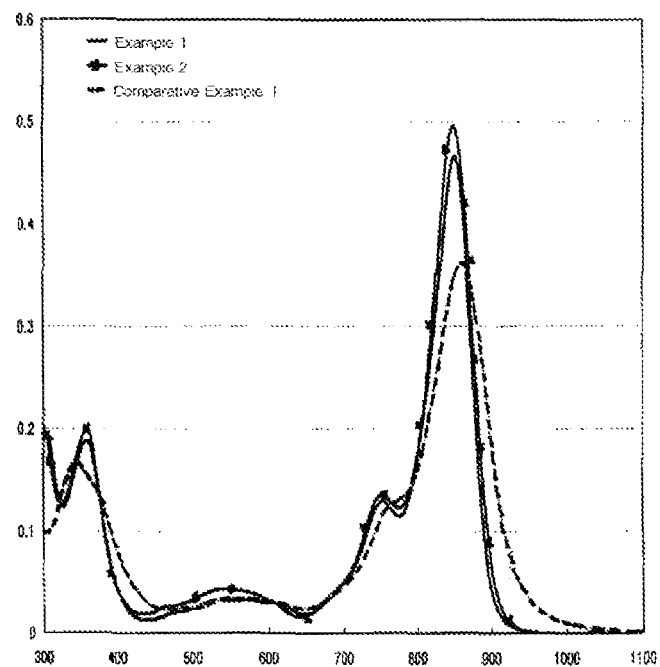
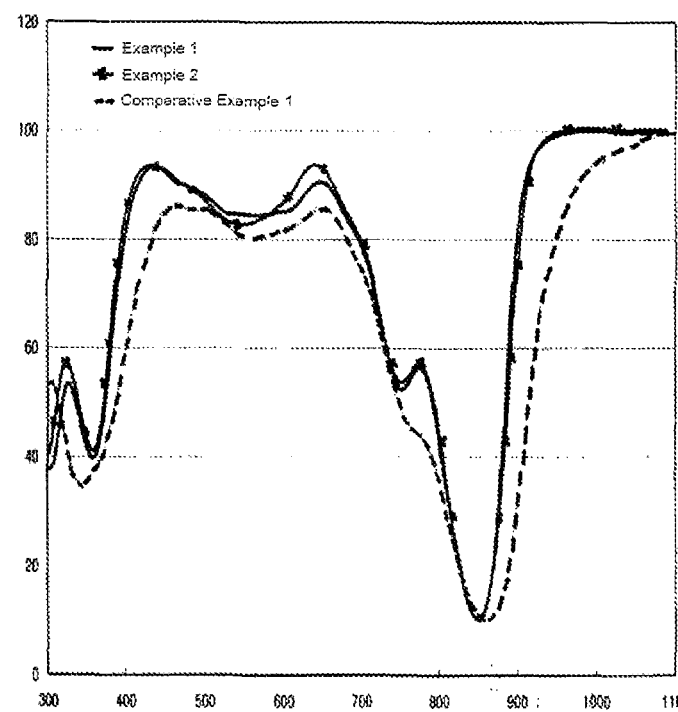
Fig. 2

COPPER PHTHALOCYANINE COMPOUNDS AND NEAR-INFRARED ABSORPTION FILTER USING THE SAME

TECHNICAL FIELD

This invention relates to a copper phthalocyanine compound and a near-infrared absorption filter using the same, and more particularly to a novel copper phthalocyanine compound with low absorptivity in the visible wavelength region and high absorptivity in the near-infrared wavelength region, and a near-infrared absorption filter using the same.

BACKGROUND ART

Phthalocyanine compounds have superior thermal and chemical stability by its structural characteristics, and changeable absorption property by metallic element introduced in the center of compound structure or characteristic group substituted at outer of compound structure. Thus, the phthalocyanine compounds are being applied in various fields such as pigments for CD, pigments applied in organic photo conductor for laser print, near-infrared absorption pigments of near-infrared absorption filter for display such as PDP (plasma display), pigments for solar cell, and so on, as well as pigments as a specific purpose. Recently, among the applications, the usage as near-infrared absorption pigments of near-infrared absorption filter for PDP is sharply increasing by rapid expansion of the display industry.

A near-infrared absorption pigment for PDP must have high light absorption property in the region of 800 to 950 nm, and low light absorption property in the visible light region, namely high transmittance, to improve color gamut (color reproductivity) of display devices. As the near-infrared absorption pigment, not only phthalocyanine compound but also various compounds such as cyanine based compounds, nickel-dithionyl based compounds, diimonium based compounds and so on, can be used. However, the cyanine based compounds are difficult to be applied actually because of lack of heat resistance, and the diimonium based compounds are limited in application because of lack of durability to the environment such as moisture, and not suitable for the near-infrared absorption filter of coating type which is being used recently. Also, the nickel-dithionyl based compounds are mainly used as sub materials, not as main materials, because of low solubility, even though they have an advantage of low light absorption property in the visible light region.

Phthalocyanine compounds have superior characteristics in all respects of durability, weather resistance and solubility, and high absorptivity in the maximum absorption wavelength of the near-infrared light region. Therefore, the phthalocyanine compounds are especially useful as a coating type near-infrared absorption pigment for PDP, and being used in various uses. Conventional phthalocyanine compounds have superior photosensitive characteristic in the region of 900 to 1000 nm, but light absorptivity in the visible light region is higher than nickel-dithionyl based compounds and so on, and light absorptivity in the region of 800 to 900 nm and the region of long wavelength over 1000 nm is not enough. Recently, the maximum absorption wavelength of the phthalocyanine compound is shifted to long wavelength region by using various central metals, but the light absorption in the region of 800 to 900 nm is insufficient. Moreover, in the case that a substituent such as a phenol, a thiophenol, first amine, and so on is introduced to shift the maximum absorption wavelength to long wavelength region or the region of 800 to 900 nm, the light absorptivity in the visible light region is increased, thus, visible light transmittance and color gamut are decreased, and applications are limited.

DISCLOSURE

Technical Problem

Therefore, it is an object of the present invention to a provide copper phthalocyanine compound with high absorptivity in the near-infrared light region, especially the region of 830 to 860 nm, and low absorptivity in the visible light region, which can provide superior color gamut (color reproductivity).

It is another object of the present invention to provide a near-infrared absorption filter using the copper phthalocyanine compound which can have superior near-infrared absorption property and color gamut.

Technical Solution

In order to achieve these objects, the present invention provides a near-infrared absorption copper phthalocyanine compound represented by following Formula 1.

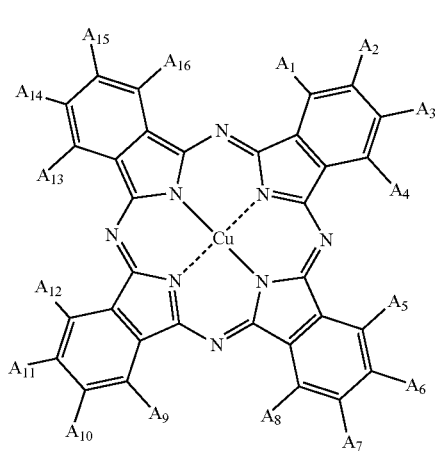

[Formula 1]

In Formula 1, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least two thereof are $NR_3R_4$, and at least four thereof are $OR_1$; $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms.

The present invention also provides a near-infrared absorption filter which comprises the near-infrared absorption copper phthalocyanine compound.

Advantageous Effects

A copper phthalocyanine compound according to the present invention has maximum absorptivity in the wavelength of 800 to 900 nm, particularly 840 to 860 nm. The transmittance of the compound in the visible wavelength region, for example, at 450 nm is excellent (more than 90%) when the transmittance at the wavelength of the maximum absorptivity is 10%.

DESCRIPTION OF DRAWINGS

FIG. 1 shows UV/VIS absorption spectra of copper and vanadium phthalocyanine compounds prepared in Example 1 and 2 and Comparative Example 1.

FIG. 2 shows UV/VIS transmission spectra of copper and vanadium phthalocyanine compounds prepared in Example 1 and 2 and Comparative Example 1.

MODE FOR INVENTION

A more complete appreciation of the invention, and many of the attendant advantages thereof, will be better appreciated by reference to the following detailed description.

A copper phthalocyanine compound in the present invention is a near-infrared absorption compound whose light absorptivity in the near-infrared wavelength region is superior and light absorptivity in the visible wavelength region is low, and is represented by following Formula 1.

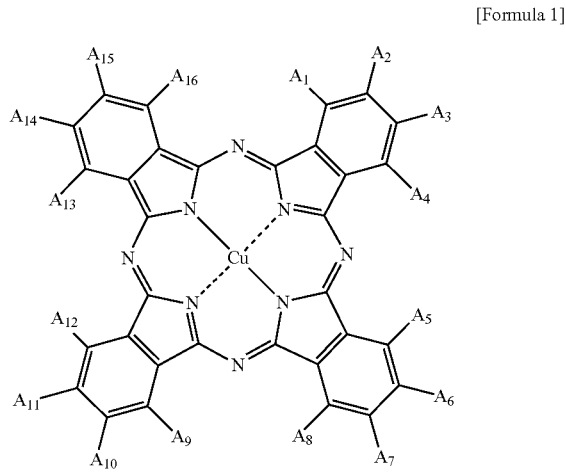

[Formula 1]

In Formula 1, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least two thereof are $NR_3R_4$, and at least four thereof are $OR_1$; $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms. $R_3$ and $R_4$ can be connected to each other to form a cyclic structure.

The preferable example of the halogen atom is a fluorine atom, and preferably, at least one of the $A_1$ to $A_{16}$ is a fluorine atom or $NR_3R_4$. Also, it is preferable that $R_3$ and $R_4$ are connected to each other to form a cyclic structure, and in this case, $NR_3R_4$ can form a heterocyclic compound of 4 to 20 carbon atoms, preferably, 4 to 8 carbon atoms such as pyrrolidine, piperidine, and so on. Also, if necessary, $R_1$, $R_2$, $R_3$ and $R_4$ can have a substituent such as an alkyl group of 1 to 10 carbon atoms, a halogen group, and so on.

The phthalocyanine compound of Formula 1, can block the light of wavelength of 800 to 900 nm by introducing a copper as a central metal in the phthalocyanine structure, and can effectively block the light of the near-infrared light region, especially the region of 830 to 960 nm and have high transmission ability of visible light by introducing a secondary amine as a substituent. Therefore, the phthalocyanine compound has superior durability and weather resistance, and a characteristic that light absorption ability in the near-infrared light region of 800 to 900 nm wavelength is superior and light absorption in the visible light region is very low. Particularly, the phthalocyanine compound has 90% or more transmittance (T %) in the visible light region (wavelength of about 450 nm) when its transmittance at the maximum absorption wavelength in the near-infrared light region (wavelength of 800 to 900 nm) is 10%.

As well known by various papers or patents, the phthalocyanine compound of Formula 1 can be synthesized by reaction of a substituted dicyanobenzene or a substituted diimino isoindoline with suitable catalyst at high temperature. For example, as disclosed in papers and patents such as Inorg. Chem. 1995, 34, 1636-1637, Japanese patent publication No. 1997-316049, and so on, the phthalocyanine compound can be prepared from substituted dicyanobenzene.

The phthalocyanine compound according to the present invention can be used for preparation of near-infrared absorption filter, as the pigment of near-infrared absorption filter, according to a conventional method. As a polymer resin for near-infrared absorption filter, most transparent polymer resins such as polymethyl methacrylate, polyester, polycarbonate, polyurethane and so on can be used. But according to each application, material suitable for required conditions such as heat resistance, weather resistance and so on is used. The near-infrared absorption filter can be prepared by coating the solution made by dissolving the near-infrared absorption pigment in solvent, on the polymer resin. As the solvent, various solvent such as methylethylketone, tetrahydrofuran, chloroform, toluene, and so on, can be used.

Hereinafter, the preferable examples are provided for better understanding of the present invention. However, the present invention is not limited by the following examples.

Example 1

Preparation of Copper Phthalocyanine 10 g of copper phthalocyanine (CuPc) precursor compound CuPc $(2,5\text{-}Cl_2PhO)_8\{2,6\text{-}(CH_3)_2PhO\}_4F_4$ (wherein, Ph=phenyl) whose UV/VIS maximum absorption wavelength is 720 nm and absorption coefficient ($\epsilon$) is 73,600 ml/g·cm, was added into a 3 neck flask having reflux condenser, and reacted with 200 ml of piperidine at 60☐ for 2 hours. After completion of the reaction, reaction solution was vacuum-evaporated to obtain copper phthalocyanine compound CuPc $(2,5\text{-}Cl_2PhO)_8\{2,6\text{-}(CH_3)_2PhO\}_4(C_5H_{10}N)_4$. Wherein, at least two of —$C_5H_{10}N$ were positioned at $A_1$, $A_4$, $A_5$, $A_8$, $A_9$, $A_{12}$, $A_{13}$ and $A_{15}$ of Formula 1. The maximum absorption wavelength of the copper phthalocyanine compound was 850 nm, and the absorption coefficient of the copper phthalocyanine compound was 53,900 ml/g·cm.

Example 2

Preparation of Copper Phthalocyanine

Except for using 200 ml of pyrrolidine instead of using 200 ml of piperidine, copper phthalocyanine compound CuPc $(2,5\text{-}Cl_2PhO)_8\{2,6\text{-}(CH_3)_2PhO\}_4(C_4H_8N)_4$ was obtained according to the same manner of Example 1. The maximum absorption wavelength of the copper phthalocyanine compound was 849 nm and the absorption coefficient of the copper phthalocyanine compound was 57,300 ml/g·cm.

Comparative Example 1

Preparation of Vanadium Phthalocyanine

Except for using vanadium phthalocyanine (VOPc) precursor compound VOPc $(2,5\text{-}Cl_2PhO)_8\{2,6\text{-}(CH_3)_2PhO\}_4F_4$ which comprises vanadium instead of copper as a central metal, and using 200 ml of pyrrolidine instead of using 200 ml of piperidine, vanadium phthalocyanine compound VOPc $(2,5\text{-}Cl_2PhO)_8\{2,6\text{-}(CH_3)_2PhO\}_4(C_6H_5CH_2NH)_4$ was obtained according to the same manner of Example 1. The maximum absorption wavelength of the vanadium phthalocyanine compound was 860 nm and the absorption coefficient of the vanadium phthalocyanine compound was 41,800 ml/g·cm.

Experimental Example

Analysis of UV/VIS Spectrum

Each of the copper and vanadium phthalocyanine compounds prepared by Example 1 and 2 and Comparative Example 1 was diluted with toluene by 10 ppm, and their UV/VIS spectra were measured. UV/VIS absorption spectra of the copper and vanadium phthalocyanine compounds prepared by Example 1 and 2 and Comparative Example 1 are shown in FIG. 1, from which maximum absorption wavelength and absorption coefficient (ml/g·cm) were calculated. Also, UV/VIS transmission spectra of the copper and vanadium phthalocyanine compounds prepared by Example 1 and 2 and Comparative Example 1 are shown in FIG. 2, which maximum absorption wavelength in the near-infrared light region and transmittance in the visible light region, namely 450 nm were calculated from and shown in the following Table 1. Wherein, the transmittance in the visible light region means the transmittance in the case that transmittance at the maximum absorption wavelength is fixed to 10%.

TABLE 1

|  | Transmittance (450 nm) | Transmittance (maximum absorption wavelength) |
| --- | --- | --- |
| Example 1 | 92.8% | 10% (850 nm) |
| Example 2 | 92.4% | 10% (849 nm) |
| Comparative Example 1 | 85.3% | 10% (860 nm) |

As shown in Table 1, the copper phthalocyanine compounds of Example 1 and 2 have superior transmittance in the visible light region, compared with the vanadium phthalocyanine compound of Comparative Example 1.

The invention claimed is:

1. A near-infrared absorption copper phthalocyanine compound represented by the following Formula 1,

[Formula 1]

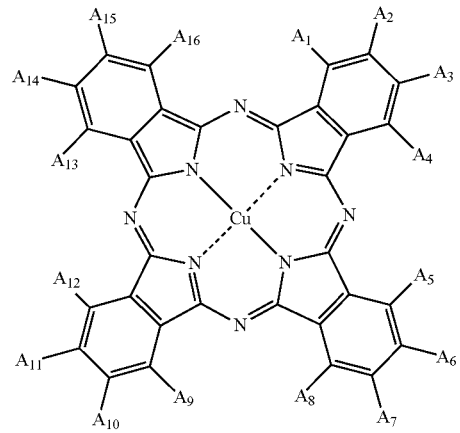

wherein, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least two thereof are $NR_3R_4$, and at least four thereof are $OR_1$; and $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms.

2. A near-infrared absorption copper phthalocyanine compound represented by the following Formula 1,

[Formula 1]

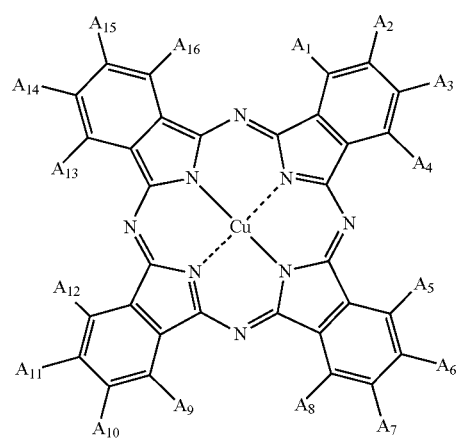

wherein, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least two thereof are $NR_3R_4$, and at least four thereof are $OR_1$; and $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms, and wherein, $R_3$ and $R_4$ are connected to form a cyclic structure.

3. A near-infrared absorption copper phthalocyanine compound represented by the following Formula 1,

[Formula 1]

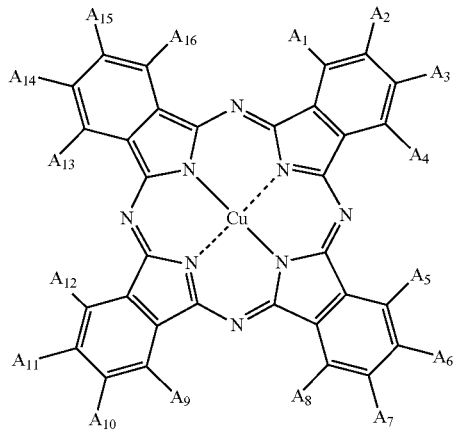

wherein, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least two thereof are $NR_3R_4$, and at least four thereof are $OR_1$; and $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms, and wherein, $NR_3R_4$ forms a heterocyclic compound whose structure is selected from the group consisting of pyrrolidine and piperidine.

4. A near-infrared absorption filter comprising:
the near-infrared absorption copper phthalocyanine compound of claim 1, and
a polymer resin,
wherein the near-infrared absorption filter is prepared by coating a solution made by dissolving the near-infrared copper phtahlocyanine compound in a solvent on the polymer resin.

5. The near-infrared absorption copper phthalocyanine compound of claim 1, wherein the copper phtahlocyanine compound has a transmittance of more than 90% in the visible wavelength and a transmittance of 10% at the wavelength of maximum absorptivity in the region of 800 to 900 nm.

6. The near-infrared absorption copper phthalocyanine compound of claim 5, wherein the copper phtahlocyanine compound has a transmittance of more than 90% in the visible wavelength and a transmittance of 10% at the wavelength of maximum absorptivity in the region of 840 to 860 nm.

* * * * *